(12) United States Patent
Maki et al.

(10) Patent No.: US 7,139,597 B2
(45) Date of Patent: Nov. 21, 2006

(54) LIVING BODY LIGHT MEASURING DEVICE

(75) Inventors: Atsushi Maki, Fuchu (JP); Tsuyoshi Yamamoto, Kawagoe (JP)

(73) Assignee: Hitachi, Ltd., Tokyo (JP)

(*) Notice: Subject to any disclaimer, the term of this patent is extended or adjusted under 35 U.S.C. 154(b) by 539 days.

(21) Appl. No.: 10/762,498

(22) Filed: Jan. 23, 2004

(65) Prior Publication Data
US 2004/0171919 A1 Sep. 2, 2004

(30) Foreign Application Priority Data
Feb. 28, 2003 (JP) ............................. 2003-052600

(51) Int. Cl.
A61B 5/00 (2006.01)
(52) U.S. Cl. .................. 600/310; 600/328; 600/336
(58) Field of Classification Search ................ 600/310, 600/322, 323, 326, 328, 336, 559; 128/897, 128/898
See application file for complete search history.

(56) References Cited
U.S. PATENT DOCUMENTS
4,195,626 A * 4/1980 Schweizer .................. 600/587

| | | | |
|---|---|---|---|
| 5,803,909 A | 9/1998 | Maki et al. | |
| 5,853,370 A | 12/1998 | Chance et al. | |
| 6,408,198 B1 | 6/2002 | Hanna et al. | |
| 6,519,486 B1 | 2/2003 | Edgar, Jr. et al. | |

FOREIGN PATENT DOCUMENTS
JP 57-115232 7/1980
JP 63-275323 5/1987

* cited by examiner

Primary Examiner—Eric F. Winakur
Assistant Examiner—Jack Lin
(74) Attorney, Agent, or Firm—Reed Smith LLP; Stanley P. Fisher, Esq.; Juan Carlos A. Marquez, Esq.

(57) ABSTRACT

There has been no device for measuring changes in Hb concentrations associated with activities of the cerebral function of an infant or subject prone to movement during measurement. Removing and reducing any influences of body movement is needed. In the present invention, light is irradiated on the subject's head, and changes in Hb concentrations associated with activities of the cerebral function are measured from scattered light which has passed through the head. From this blood circulation movement, a parameter is inputted arbitrarily to judge the body movement component, and feed-back is applied to a stimulus device for giving a stimulus to the subject.

9 Claims, 12 Drawing Sheets

FIG. 3

[PROCESSING 1] LOAD DATA FROM MEMORY

[PROCESSING 2]
- OPERATE VARIOUS HEMOGLOBIN (Hb) CHANGE DATA $\Delta C(t)$.
- APPLY BAND PASS FILTER WHICH PASSES THROUGH, FOR EXAMPLE, 0.021 Hz TO DETERMINE $\Delta C_{bp}(t)$ BY OPERATION (FOURIER TRANSFORM METHOD, WAVELET TRANSFORM METHOD, CONVOLUTION METHOD OR THE LIKE IS USED)
- AS REGARDS PASSING BAND, AUTOMATICALLY SET WITH ADAPTIVE FILTER, OR OPERATOR CAN ARBITRARILY SET ON SCREEN (SEE FIG. 3, FIG. 4)

[PROCESSING 3] FROM $\Delta C(t)$ AND $\Delta C_{bp}(t)$, TAKE BLOCK DATA $\Delta C(t, n)$ AND $\Delta C_{bp}(t, n)$ USING TIMING OF STIMULUS MARK AS A REFERENCE. AT THIS TIME, WHEN STIMULUS IS EXPOSED TO SUBJECT TEN TIMES, $n = 1$ TO $10$.

[PROCESSING 4] TAKE AWAY BLOCK INCLUDING $\Delta C_{bp}(t, n)$ BODY MOVEMENT NOISE. SINCE BODY MOVEMENT CRITERION VALUE OF JUDGMENT VARIES WITH IRRADIATION DETECTION DISTANCE AND INDIVIDUAL, IT IS ALSO POSSIBLE TO ARBITRARILY INPUT.

[PROCESSING 5] CORRECT BASE LINE AND CHANGE THE OFFSET VALUE OF DATA $\Delta C_{bp}(t, n)$ FOR EACH BLOCK TO DETERMINE $\Delta C_{bp\_correct}(t, n)$.

[PROCESSING 6] ADD AND AVERAGE TO OBTAIN $\Delta C_{bp\_correct}(t, n)$ IN ORDER TO DISPLAY RESULT.

DEFINITION OF TIME AND DEFINITION OF STIMULUS BLOCK

STIMULUS TIMING ACTUALLY GIVEN DURING MEASUREMENT

STIMULUS TIMING TO BE USED FOR ARITHMETIC EVALUATION OF RESULT

CHANGES IN Hb CONCENTRATIONS WHEN LISTENING LANGUAGE
(WITH BODY MOVEMENT CORRECTION)

CHANGES IN Hb CONCENTRATIONS WHEN LISTENING LANGUAGE
(WITHOUT BODY MOVEMENT CORRECTION)

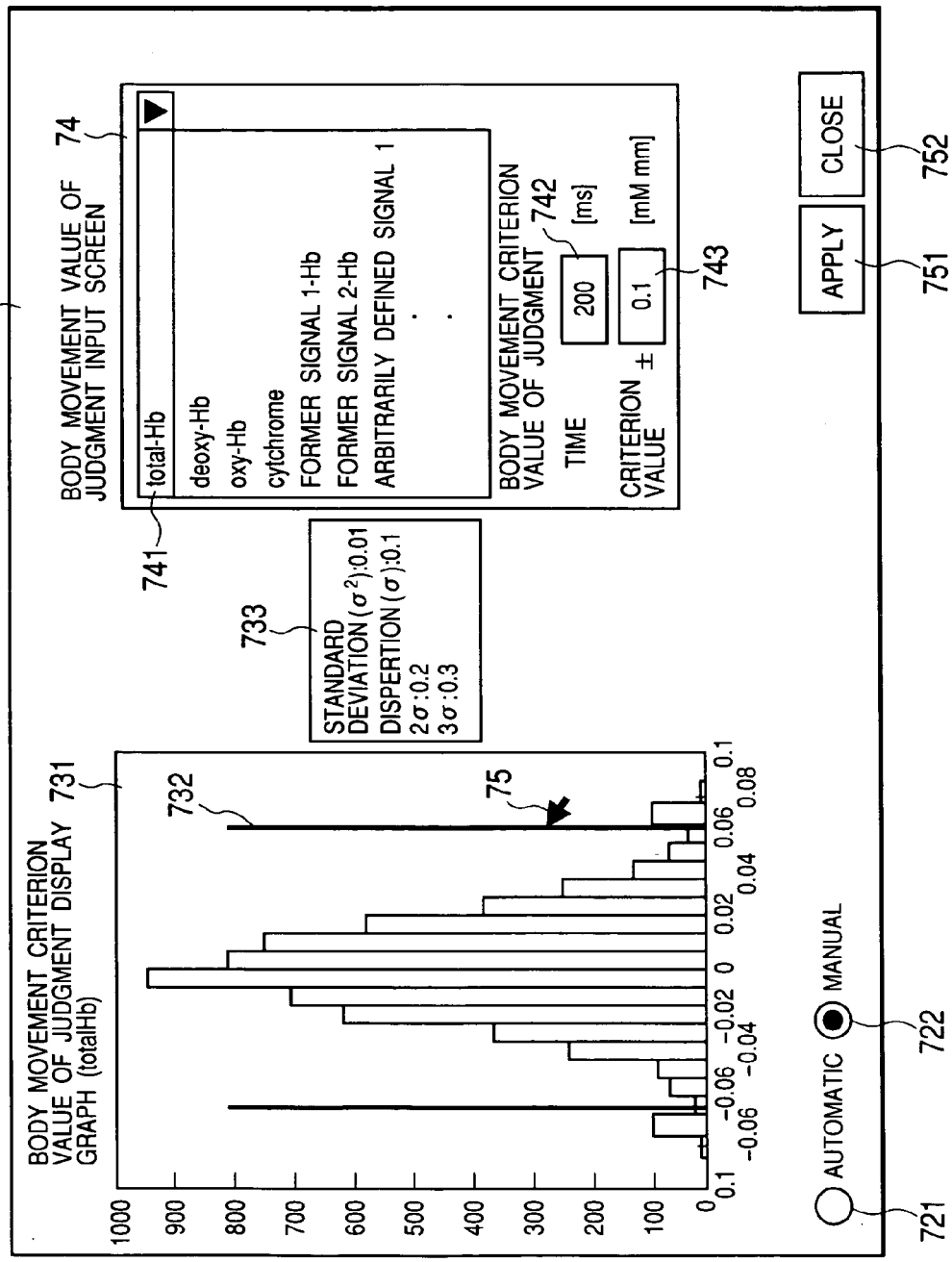

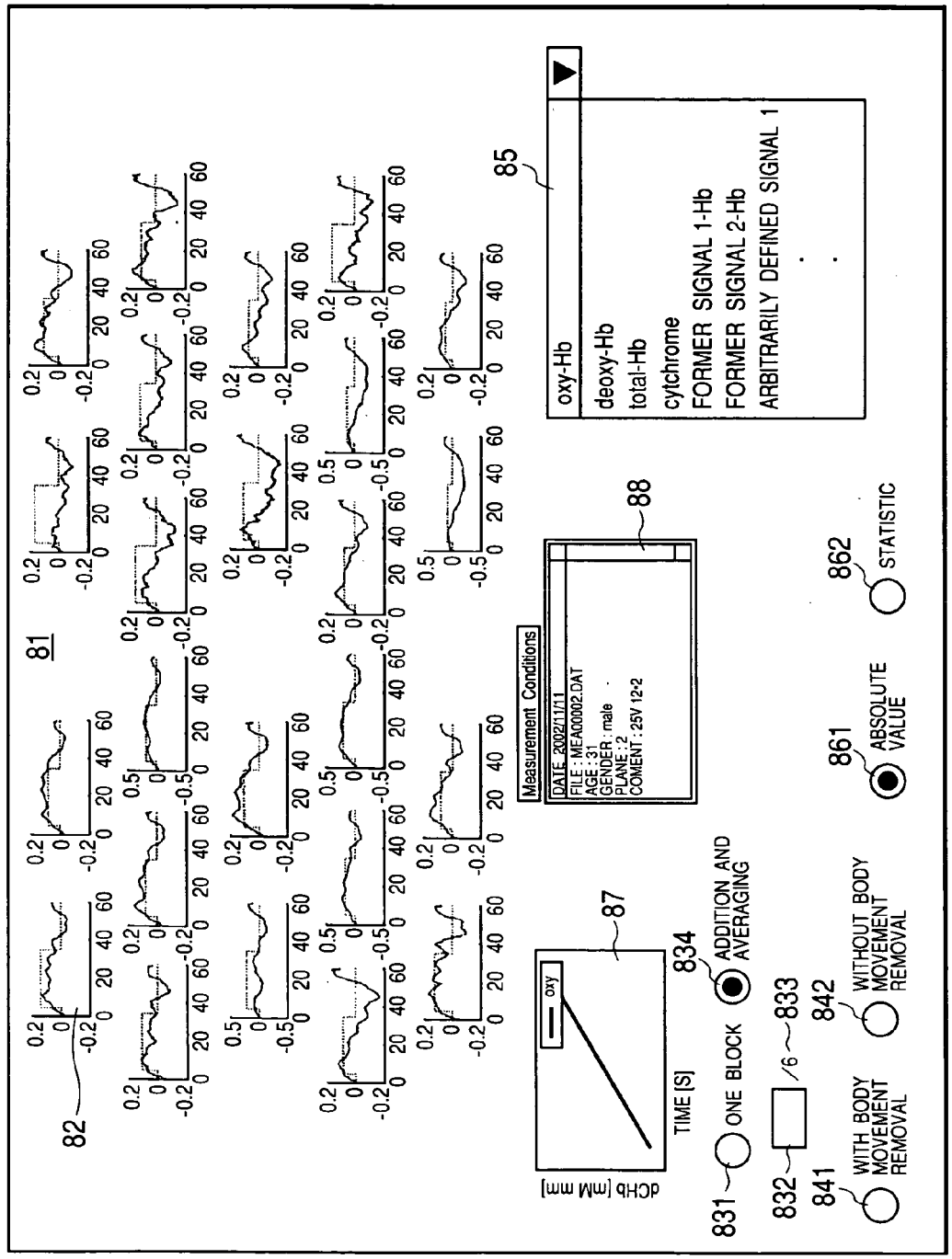

STIMULUS TIMING ACTUALLY GIVEN DURING MEASUREMENT

STIMULUS TIMING TO BE USED FOR ARITHMETIC EVALUATION OF RESULT

STIMULUS TIMING ACTUALLY GIVEN DURING MEASUREMENT

STIMULUS TIMING TO BE USED FOR ARITHMETIC EVALUATION OF RESULT

LIVING BODY LIGHT MEASURING DEVICE

PRIORITY CLAIM

This application claims priority under 35 U.S.C. §119 to Japanese patent application P2003-052600 filed Feb. 28, 2003 the entire disclosure of which hereby is incorporated herein by reference.

FIELD OF THE INVENTION

The present invention relates to a device for measuring human cerebral function without affecting it.

BACKGROUND OF THE INVENTION

Thus far, as a method for measuring human cerebral function, there has been a technique for measuring activities of a cerebral cortex through the use of light.

In bio-instrumentation using light, a device for measuring a living body function using visible light to near infrared light has been disclosed in, for example, Patent Document 1, Japanese Patent Laid-Open No. 115232/1982, or Patent Document 2, Japanese Patent Laid-Open No. 275323/1988. Further, an invention concerning an image measurement technique for a cerebral function which uses the present principle of measurement has been disclosed in Patent Document 3, Japanese Patent Laid-Open No. 1997/98972.

These use such light wave-guides as represented by optical fiber or the like to converge light (hereinafter abbreviated as living body passage light) which by irradiating light on a living body, has permeated through at a position apart by several mm to several cm while being scattered within the living body for measuring. From intensity of the living body passage light measured, such a concentration of photoabsorption substance within the living body as represented by oxygenation hemoglobin, deoxidation hemoglobin and the like or a value corresponding to the concentration will be determined. When determining the concentration of photoabsorption substance or the value corresponding to the concentration, a photoabsorption characteristic of the photoabsorption substance aimed at, corresponding to wave length of the light irradiated will be used. Generally, when measuring the depth of the living body from the surface of the living body, there will be used light having wave length within a range of 650 nm to 1300 nm which has high living body permeability.

SUMMARY OF THE INVENTION

Thus far, when measuring an advanced function resulting from activities of the cerebral cortex by the above-described method using the living body passage light, if a subject does not stand still, a signal obtained by measuring will have enormous noise levels associated with body movement, and it has been difficult to analyze the signal. When a healthy adult or the like becomes a subject, it is not so difficult to cause the subject to stand still, but when an infant, an elderly person or the like becomes a subject, the subject cannot stand still consciously in sufficient measure. Therefore, it is an important problem in order that the light measurement method becomes usable even for moving subjects to develop a measuring method and a signal processing method when the subject moves.

If this problem is solved, it will become possible to measure the cerebral function of an infant or the like, and to detect any disorder in an advanced function during an infant period in its early stages. The disorder in the advanced function is, in the case of, for example, language, often detected when it is two or three years old in which the subject begins talking. In such a case, language acquisition will be delayed as compared with a normal case, and enormous efforts will be required in order to recover from the delay in diagnosis.

Therefore, it is strongly demanded socially to develop a method or a device capable of measuring a disorder in the advanced cerebral function in the early stages, and it is a problem which should be solved.

In the present invention, for example, a language/hearing sense stimulus is given to a subject, and presence or absence of any disorder in an advanced function of an infant will be measured by a measuring method using light. At this time, a noise due to body movement will be automatically detected from the measurement signal to be removed.

Since it is a pulsive noise, the noise due to body movement has a broad band in the frequency domain. For this reason, it is difficult to remove it by a simple frequency filter. Accordingly, in the time domain, an amount of change at an arbitrary time interval will be determined by a computation to automatically judge a component of the body movement, that is, a component of the body movement noise of the data obtained, from the amount of change.

Also, normally, in the measurement of the cerebral function, its changes are often statistically evaluated, and in order to secure their statistical accuracy, the same stimuli will be given to the same subject two or more times. Further, when comparing with another subject, in order to evaluate the statistics at the same standard, it is preferable to give the same number of times of stimuli to all the subjects. In the present invention, even this problem has been solved by judging body movement noise in real time to apply a feedback to the number of times of stimuli.

BRIEF DESCRIPTION OF THE DRAWINGS

FIG. 3 is a view showing an example of a signal processing flow for a signal measured according to the present invention;

FIG. 8 is a view showing an example of a body movement criterion of judgment setting screen for setting a criterion for judging that there is included a body movement component;

FIG. 9 is an example of a screen showing results obtained by eliminating noise on the basis of the body movement criterion of judgment due to the screen of FIG. 8;

DETAILED DESCRIPTION OF THE PREFERRED EMBODIMENTS

First Embodiment

Figure 1:
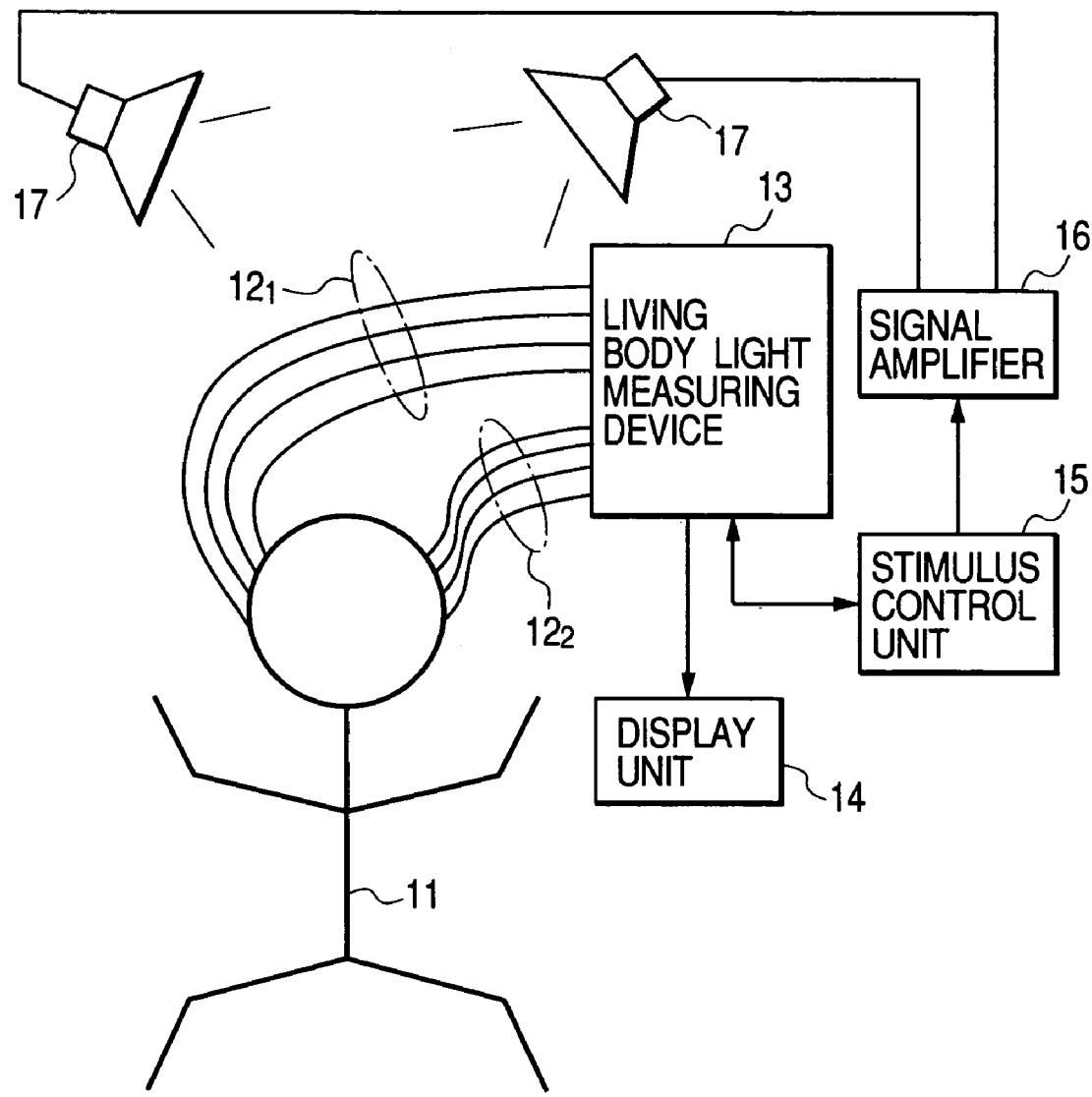
FIG. 1 is a view showing structure of a device according to a first embodiment of the present invention.

With reference to FIG. 1, the description will be made of the structure of the device of the first Embodiment of the present invention.

Figure 2:
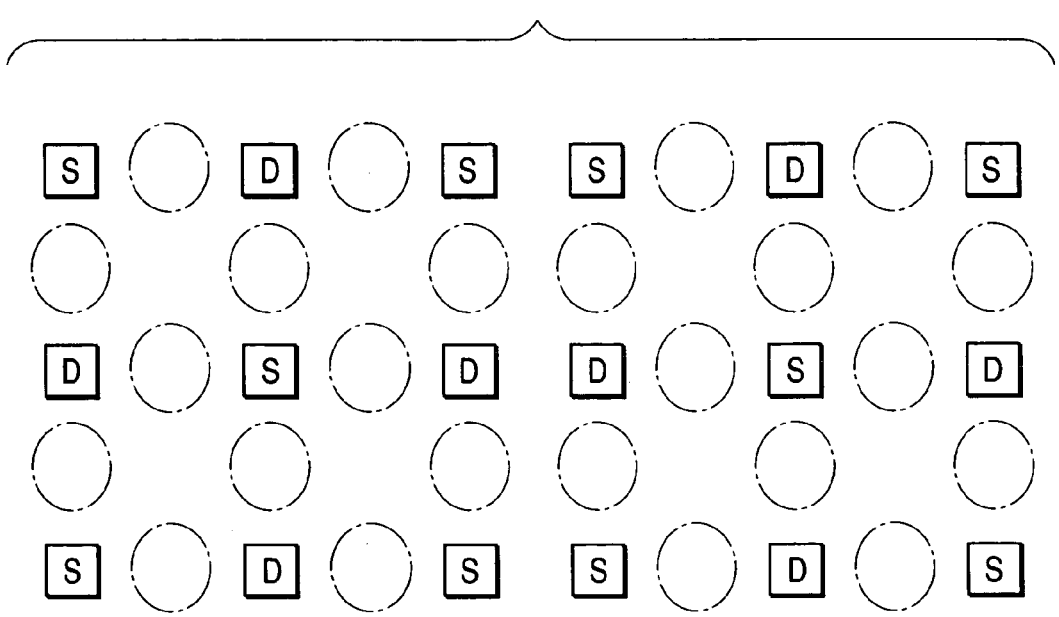
FIG. 2 is a view showing an example of arrangement of optical fiber for irradiation and optical fiber for light convergence.

In a state in which an infant 11 is quietly lying on a bed or the like, measurement will be performed. On the head of the infant 11, a plurality of optical fibers 12 are fitted. For the optical fibers, there are optical fibers $12_1$ (light irradiation means) for irradiation for irradiating light from each of light sources from above the head skin, and optical fibers $12_2$ (for light convergence and detection) for light convergence for converging scattered light which has passed through the interior of the living body to a wave-guide into a detector for measuring a domain with a fixed area by their combination. Here, the optical fibers $12_1$ for irradiation and the optical fibers $12_2$ for light convergence have been schematically shown in a state in which these two are spaced apart, but these are ordinarily arranged to be alternately dispersed in a domain with a fixed area. This one example is shown in FIG. 2. In FIG. 2, S corresponds to a position of the optical fibers $12_1$ for irradiation, and D corresponds to a position of the optical fibers $12_2$ for light convergence respectively. When arranged in this way, scattered light which has passed through the interior of the living body in a domain shown by enclosing with a dot-and-dash line sandwiched between the optical fibers $12_1$ S for irradiation and the optical fibers $12_2$ D for light convergence is detected through the optical fibers $12_2$ for light convergence. Light to be normally irradiated is near infrared light having as high biological permeability as close to 800 nm. From a value of this near infrared light to be absorbed within the living body, an amount corresponding to concentration changes of hemoglobin (Hb) can be measured. In this case, the concentration indicates Hb molecular weight in the unit tissue. Since for Hb, there are oxygenation oxy-Hb for carrying oxygen and deoxidation deoxy-Hb from which oxygen has separated, when each of them is separated for being measured, two wave length adequate for each are selected for measurement. In this case, total Hb (total-Hb) concentration changes, which is the sum total of the oxy-Hb concentration changes and deoxy-Hb concentration changes corresponds to changes in amount of blood.

It has been known that activity of adult's cerebral function, a change in amount of blood, oxy-Hb concentration changes, and deoxy-Hb concentration changes (hereinafter, collectively called changes in Hb concentrations) have close relationships. This is because when activities of cerebral function occur, metabolism accelerates in a local domain within brain for bearing the function; in order to feed oxygen to the domain, the amount of blood and oxy-Hb concentration are locally increased and the deoxy-Hb concentration is reduced. Therefore, the change in amount of blood, the oxy-Hb concentration changes and the deoxy-Hb concentration changes are measured, whereby it is possible to know the activity of adult's cerebral function. So far, it has been known that it is possible (See Patent Document 1) to measure or image the activity of adult's cerebral function by a method using the near infrared light.

As regards the changes in Hb concentrations associated with cerebral activities of a newborn baby or an infant, however, there has been no method for measuring without giving any anesthetic or the like. For this reason, relationship between the cerebral activities of the newborn baby and the changes in Hb concentrations is unknown. Of course, the cerebral activities themselves are also unknown. In the method using light like the first Embodiment, since the optical fibers 12 are only fitted onto the head, it is possible to measure without giving an anesthetic or the like in terms of the principle.

The living body light measuring device 13 is a measuring device using this near infrared light, in which a plurality of optical fibers 12 are connected, and light sources, light detectors and the like are incorporated correspondingly to each fiber 12. The living body light measuring device 13 processes signals obtained from the optical fibers $12_2$ for light convergence to perform time series processing, imaging and the like of changes in Hb concentrations within the living body, and has, in order to display on the display unit 14, an analog-to-digital converter, a memory, and a signal processing device packaged with CPU and a necessary program although not shown.

A stimulus control device 15 is a device for controlling a stimulus to be given to the newly born baby. In this stimulus control device 15, a plurality of sound/voice/language data for stimuli have been recorded as analog or digital data. These sound, voice and language data are transmitted at arbitrary timing, are amplified by a signal amplifier 16, those sound, voice and language are produced through two or more speakers 17 to cause the infant 11 to listen. Timing at which sound, voice and language have been produced, a time period and the time, and types of sound, voice and language which have been selected are recorded in the living body light measuring device 13. Also, it may be possible to instruct by the living body light measuring device 13 concerning types of sound, voice and language which are produced as timing and stimulus conversely, and to select from among the sound, voice and language which have been stored in accordance with the instruction for issuing a signal by the stimulus control device 15. In other words, it is important that the living body light measuring device 13 and the stimulus control device 15 are synchronized.

As sound, voice or language is produced from a speaker 17, a change in blood circulation movement within the brain occurs because a language/hearing sense function of the infant 11 works. A signal obtained from the optical fibers $12_2$ for light convergence is recorded by the living body light measuring device 13 as its change in blood circulation movement. During the measurement, information and a measurement signal of the stimulus to be given to the infant from the stimulus control device 15 are displayed on the display unit 14, and after the completion of all the measurements, the signals are processed by the living body light measuring device 13 to display the result on the display unit 14.

The signals obtained by measuring by the living body light measuring device 13 shown in FIG. 1 are properly processed, whereby noise resulting from the body movement can be removed.

First, with reference to FIG. 3, the description will be made of a signal processing flow of the signal obtained by measuring. This signal processing flow can be also used as post processing after the termination of the measurement, or as real time processing while measuring.

[First Processing]: Read the measurement data from the memory. Since a signal to be obtained from the optical fibers 12₂ for light convergence is analog data concerning light intensity, the signal is replaced with a digital signal at a predetermined sampling period by an analog-to-digital converter within the living body light measuring device 13 to be stored in a memory within the living body light measuring device 13. This stored data is read out in a predetermined time unit.

[Second Processing] A concentration change $\Delta C(t)$ of hemoglobin (Hb) will be derived. With an average value during previous T1 seconds from the first stimulus presented time as a base line, $\Delta C(t)$ will be derived. In this case, $\Delta C$ designates $\Delta C_{oxy}(t)$, $\Delta C_{deoxy}(t)$ which are expressed by expression (1), and $\Delta C_{total}(t)$ to be expressed by expression (2).

[Numerical Formula 1]

$$\begin{bmatrix} \Delta C_{oxy}(t) \\ \Delta C_{deoxy}(t) \end{bmatrix} = \begin{bmatrix} \varepsilon_{oxy}^{\lambda 1} & \varepsilon_{deoxy}^{\lambda 1} \\ \varepsilon_{oxy}^{\lambda 2} & \varepsilon_{deoxy}^{\lambda 2} \end{bmatrix}^{-1} \begin{bmatrix} -\log_e \frac{T^{\lambda 1}(t)}{T_f^{\lambda 1}(t)} \\ -\log_e \frac{T^{\lambda 2}(t)}{T_f^{\lambda 2}(t)} \end{bmatrix} \quad (1)$$

[Numerical Formula 2]

$$\Delta C_{total}(t) = \Delta C_{deoxy}(t) + \Delta C_{oxy}(t) \quad (2)$$

where $T^{\lambda}$ is a transmission factor of wave length $\lambda$, t is time, oxy is oxygenation Hb, deoxy is deoxidation Hb, total is total Hb, $\varepsilon_{oxy}^{\lambda}$ is a molecular absorbance factor of oxigenation Hb in wave length $\lambda$, and $\varepsilon_{deoxy}^{\lambda}$ is a molecular absorbance factor of deoxidation Hb in wave length $\lambda$. Also, the above-described base line is expressed by expression 3.

[Numerical Formula 3]

$$T_f^{\lambda}(t) = \frac{1}{N} \sum_{t=1}^{N} T_t^{\lambda} = \text{const} \quad (3)$$

where N is a number of measurement points sampled during T1 seconds prior to the first stimulus presented time. The T1 seconds period can be arbitrarily set, and in measurements in which an effect of the present invention has been verified, N=50 is given because the measurement is made at sampling period of 100 ms and T1 has been made into 5 seconds.

When real time processing is made, this Hb data varies from moment to moment in response to measurement to be displayed on the display unit 14.

Figure 4:
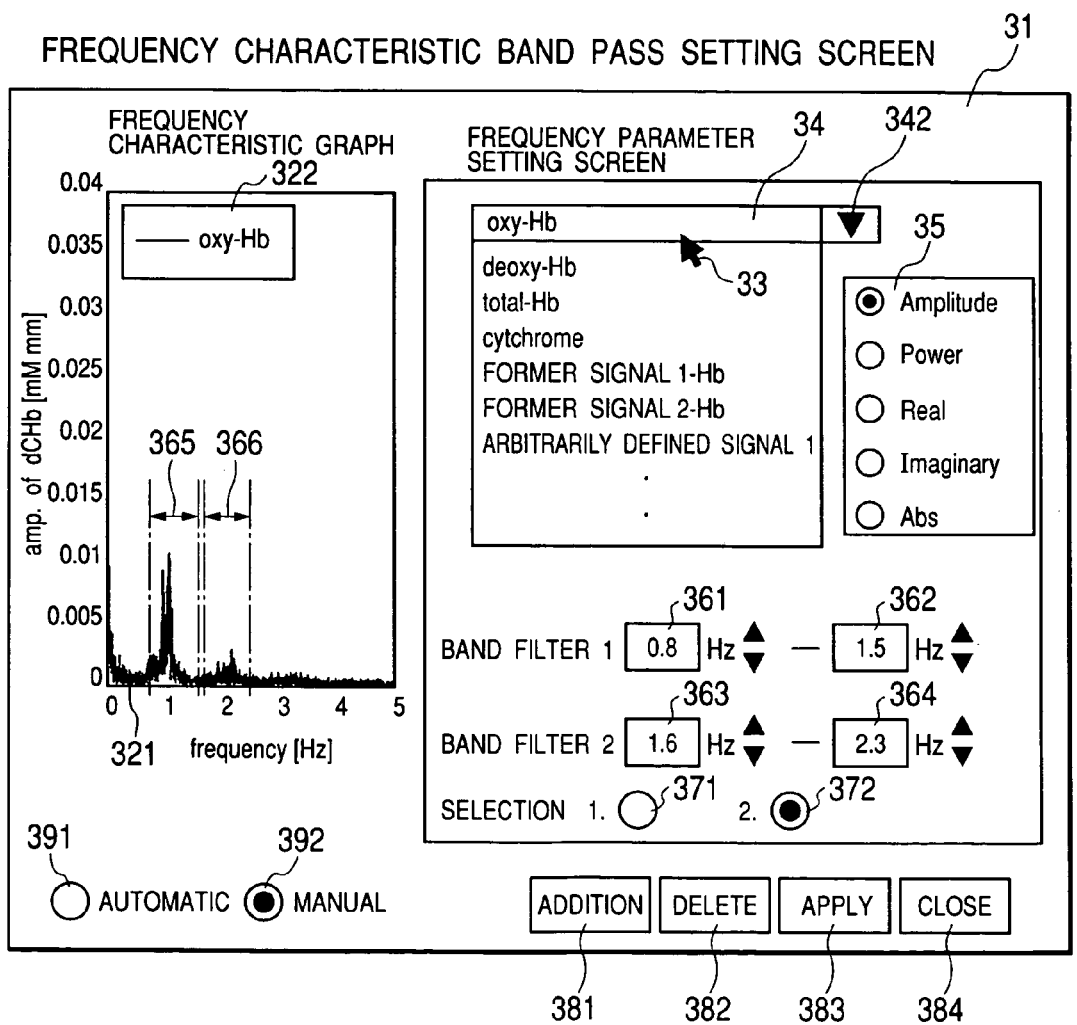
FIG. 4 is a view showing an example of a frequency characteristic setting screen of a band pass filter according to the first embodiment of the present invention.
Figure 5:
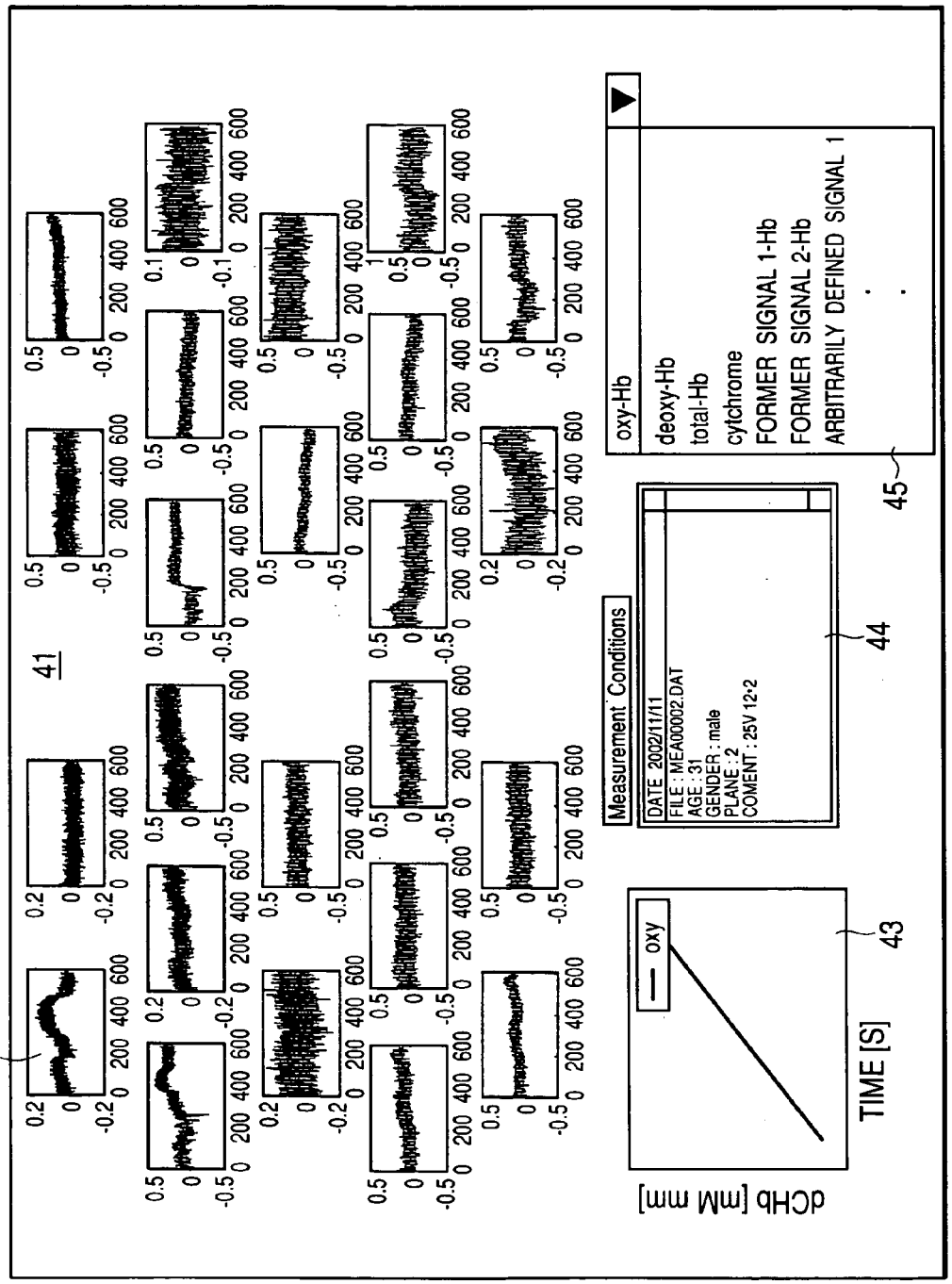
FIG. 5 is a view showing an example of results obtained by causing signals to be obtained from the optical fiber for light convergence to pass through the band pass filter set in FIG. 4.

A value of a passing frequency band of a signal to be obtained from the optical fibers 12₂ for light convergence is automatically determined by computing a adaptive filter for calculation, or a filter value set in advance can be used, and when those values should be arbitrarily set by an operator, the $\Delta C(t)$ obtained is processed by Fourier transform, wavelet transform or convolution method to arbitrarily determine a band pass filter value by taking advantage of such a frequency characteristic setting screen as exemplified in FIG. 4 to be described later. Since low-frequency noise and heart beat (newborn baby heat beat is 1.5 to about 2.2 Hz, adult heart beat is about 1 Hz) differ with the subject, automatization is often difficult, and this function enables fine correspondence. Thus, a signal $\Delta C_{bp}(t)$ which has passed through a band pass filter set automatically or arbitrarily will be determined to display as shown in FIG. 5. Details concerning FIGS. 4 and 5 will be described later. Hereinafter, data that has been obtained through the band pass filter will be attached with a numerical subscript bp to be distinguished from data that no band pass filter has been applied.

[Third Processing]: From a signal to be obtained from the optical fibers 12₂ for light convergence, data $\Delta C(t)$ that no band pass filter has been applied and data $\Delta C_{bp}(t)$ which has passed through the band pass filter will be extracted for each stimulus block. In the present embodiment, as shown in FIG. 6, one stimulus block has been defined such that time prior to stimulus (Tpre) is 5 seconds, stimulus time (Ts) is 15 seconds and post-stimulus time (Tpost) is 15 seconds, and total time for each stimulus block becomes 35 seconds. In the present measurement embodiment, stimulus for 15 seconds period (the subject is caused to listen to spoken language of its native language) is given to each subject, and between each stimulus time, rest time of about 20 seconds during which it does nothing has been given. This stimulus of 15 seconds and rest time of 20 seconds have been repeated ten times for each subject.

[Fourth Processing]: It is judged for each data of each stimulus block whether or not a body movement component is contained, and data of a stimulus block judged to contain the body movement component will be excluded from the processing object of fifth processing. A criterion value to be judged to contain body movement noise has been defined as a case where within 200 ms, total-$\Delta C_{bp}$ has changed by 0.1 mMmm or more (when irradiation-detection distance is 20 mm, 0.066 mMmm or more) when irradiation-detection distance of fiber 12 is 30 mm. Data which has passed this criterion value of judgment means that on the assumption that effective scattering distance is 1 mm, a change in amount of blood of 100% does not occur within 200 ms in the cerebral cortex. Since, however, the criterion value of judgment of body movement may fluctuate according to the circumstances (for example, when the irradiation-detection distance is changed, when a spike-shaped signal is detected through the use of wavelet transform or the like), there may be cases where it becomes necessary for the operator to change the preset value. In order to cope with this, the body movement criterion of judgment will be rendered changeable by taking advantage of a body movement criterion of judgment setting screen for setting a criterion on the basis of which it is judged that the body movement component exemplified in FIG. 8 is contained. FIG. 9 has a screen for showing a result in which noise has been removed by the body movement criterion of judgment. The details of FIGS. 8 and 9 will be described later.

Figure 6A:
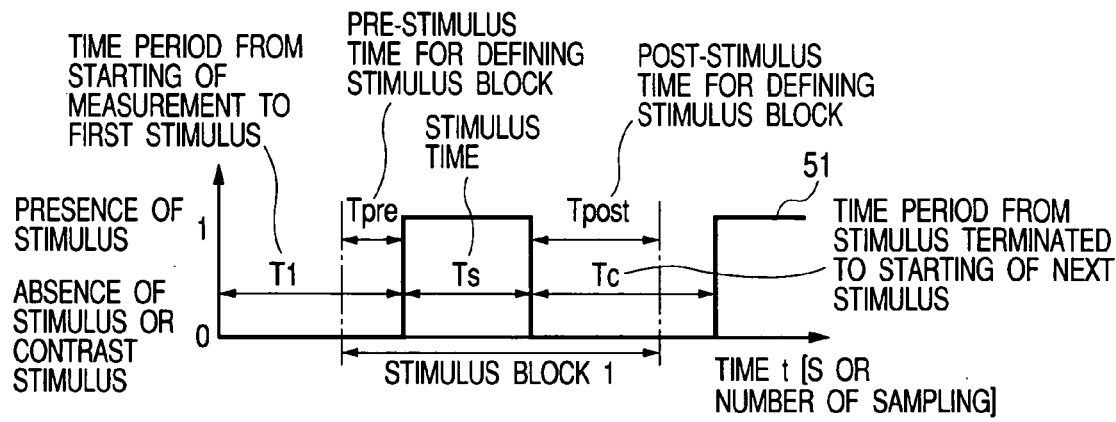
FIG. 6A, FIG. 6B, and FIG. 6C are graphs showing time definition and definition of a stimulus block, actual timing of stimulus to be given during measurement, and an example of timing of stimulus to be used for arithmetic evaluation of the result respectively.
Figure 6B:
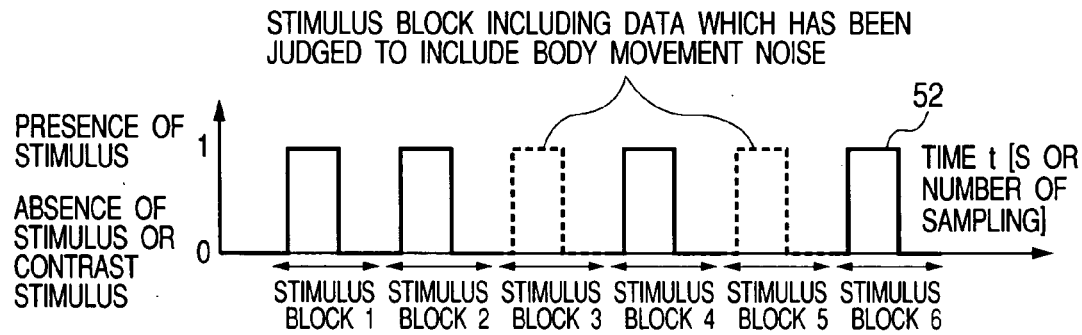
Figure 6C:
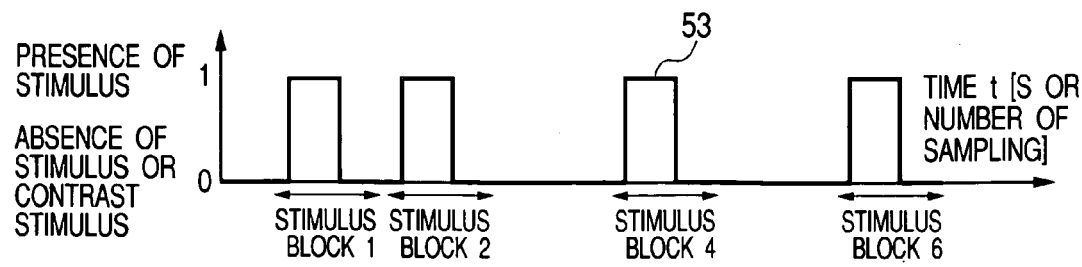

FIG. 6 shows a schematic representation of concepts of the third processing and the fourth processing. FIGS. 6A, 6B and 6C show three types of graphs: FIG. 6A shows time definition and definition of a stimulus block; FIG. 6B shows actual timing of stimulus to be given during measurement; and FIG. 6C shows timing of stimulus to be used for arithmetic evaluation of the result. In these graphs 6A, 6B and 6C, stimulus timing waveform 51, 52, 53 is displayed with time or a number of sampling taken on the abscissa, and a period in which no stimulus is given, or with a period of contrast stimulus as 0 and a period of stimulus as 1 on the ordinate.

The graph 6A represents various time definitions of stimulus timing, and during actual measurement, these T1, Ts, Tc, Tpre, and Tpost will be set. Here, the stimulus timing waveform 51 is displayed enlarged as compared with other stimulus timing waveform 52 and 53.

In the graph 6B, within a series of stimulus timing waveform 52, in order to clearly express a difference between a stimulus block in which data judged in the third processing to contain body movement noise has been obtained, and a stimulus block in which data judged to contain no body movement noise has been obtained, the former stimulus block has been displayed by a dotted line and the latter stimulus block by a solid line. Accordingly, the graph 6B shows that during the measurement, data judged to contain the body movement noise has been detected during periods of the stimulus blocks 3 and 5.

In the graph 6C, the stimulus timing waveform 52 represents that the stimulus block in which data judged to contain body movement noise has been obtained has been removed. In other words, the stimulus block in which data judged to contain body movement has been obtained is regarded as no stimulus having been given, and is excluded from processing.

[Fifth Processing]: Concerning a period $\Delta C_{bp}(t)$ of each stimulus block which has passed a criterion of judgment of the fourth processing, a base line is arbitrarily selected from polynomial of zero-order to fourth order from pre-stimulus time and post-stimulus time, and the base line is corrected through the use of the polynomial thus determined. In the case of zero-order, however, an average value of the pre-stimulus time is used as the base line. When a concentration change whose base line has been corrected is represented by $\Delta C_{13}$ correct(t) and the base line is represented by $\Delta C\_baseline(t)$, $\Delta C_{bp\_}correct(t) = \Delta C_{bp}(t) - \Delta C_{bp\_}baseline(t)$ is given.

[Sixth Processing]: Addition and averaging will be performed on data $\Delta C_{bp\_}correct(t)$ judged in the fifth processing to contain no body movement noise.

Figure 7A:
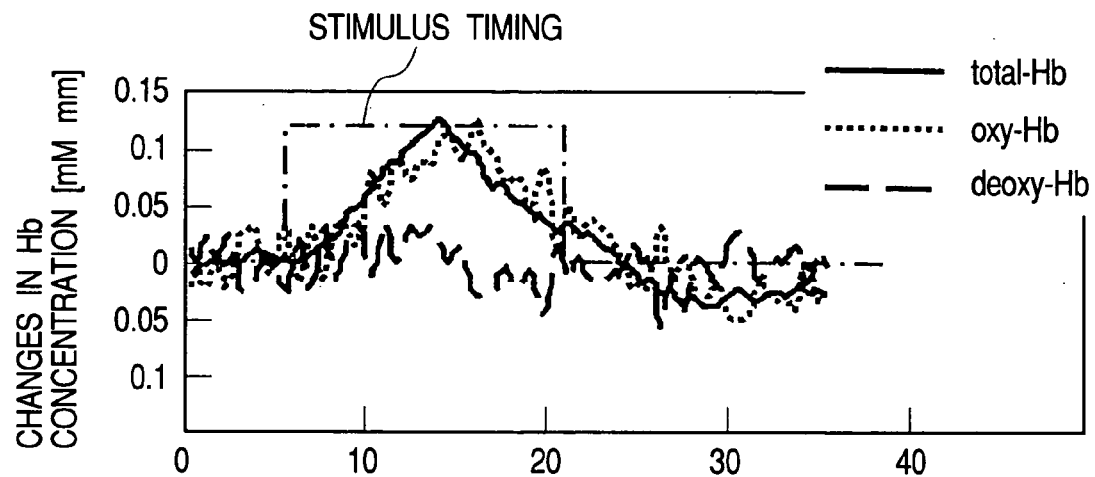
FIG. 7A and FIG. 7B are a graph showing changes in Hb concentrations within the brain obtained by performing the processing described in FIG. 3, and a view showing an example of a graph showing changes in Hb concentrations within the brain obtained by adding and averaging all signals obtained without performing the processing described in FIG. 3 for comparison respectively.
Figure 7B:
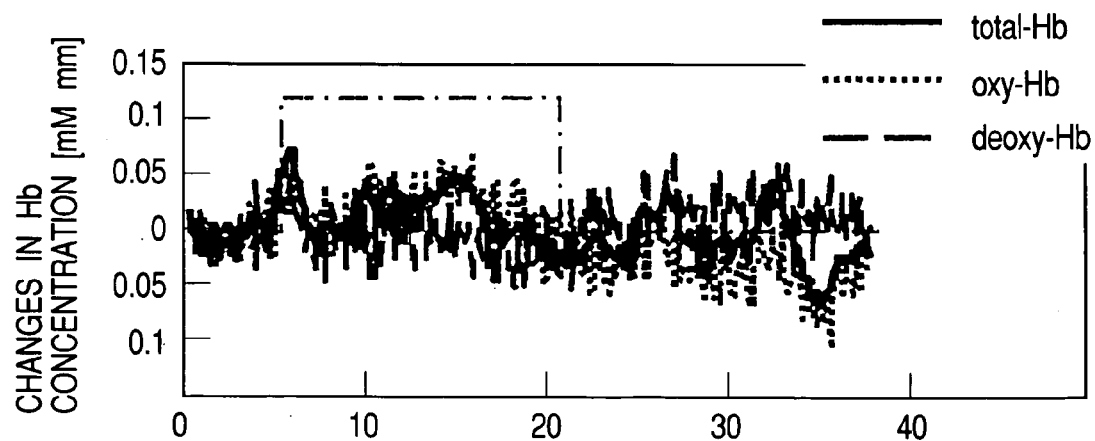

FIG. 7A is a graph showing changes in Hb concentrations within brain obtained by performing the processing described in FIG. 3. This graph shows changes in Hb concentrations within brain of a newborn baby within five days after birth, and shows changes in Hb concentrations in the temple (left hemisphere language hearing sense field) when the subject (newborn baby) is caused to listen to language at timing of stimulus indicated by a dot-and-dash line. FIG. 7B is a graph showing changes in Hb concentrations within brain obtained by adding and averaging all the signals obtained in the [Sixth Processing] without performing body movement judgment to be performed in the above-described [Third Processing] and [Fourth Processing] with respect to the same signal for comparison.

In each graph, the ordinate indicates values corresponding to concentration changes of total-Hb, oxy-Hb and deoxy-Hb, the abscissa represents time, and the dot-and-dash line represents timing at which a stimulus is given to the subject (in a period of 0, no stimulus is given, but in other periods than 0, a stimulus is given). Also, the solid line represents changes of total-Hb, the dotted line, changes of oxy-Hb, and a broken line changes of deoxy-Hb respectively. These have been obtained by adding and averaging result obtained by correcting the base line with a function of zero-order after the band pass filter is applied. That is, these display $\Delta C_{bp\_}correct(t)$ for each Hb. Although the order of the polynomial used as the base line has been compared from the first order to the fourth order, the results have been substantially the same.

When results of FIGS. 7A and 7B are compared, in a case where data of the stimulus block in which data judged to contain body movement noise has been obtained has been removed from signal processing as shown in FIG. 7A, a state in which the blood circulation movement within the brain reacts with the stimulus is inferred. In a case, however, data of the stimulus block in which data judged to contain body movement noise has been obtained has not been removed from signal processing as shown in FIG. 7B, any significant signal cannot be observed.

Therefore, from this series of processing, it can be seen that it is important to remove the signal of body movement noise, and this is indispensable as processing.

Here, the detailed description will be made of a frequency characteristic setting screen of the band pass filter shown in FIG. 4. The frequency characteristic setting screen has the following domains:
1) A domain displaying frequency characteristic of a signal to be obtained from the optical fibers $12_2$ for light convergence.
2) A domain for selecting a signal to be displayed in the above-described 1).
3) A domain for displaying type of the frequency characteristic.
4) A domain for determining a range of passing frequency of the band pass filter.
5) A domain for selecting addition, delete and application of a filter when a plurality of band pass filters have been set.
6) A button for closing a setting screen of the band pass filter, and
7) A button for selecting whether the band pass filter will be automatically set by automatically operating an adaptive filter on the basis of a preset value or it will be set arbitrarily by the operator.

In the domain displaying frequency characteristic of a signal of the above-described 1), as displayed in the figure as the frequency characteristic graph, a graph display 321 for a signal to be obtained from the optical fibers $12_2$ for light convergence, and a legend 322 for representing correspondence relationship between names of signals graph displayed and line types of graph display are displayed.

In the domain for selecting a signal to be displayed in the above-described 2), there is displayed a signal selection unit 34 which is displayed as a frequency parameter setting screen. On the signal selection unit 34, there is displayed a pull down 342 for selecting a signal to be displayed. Since by depressing the pull down 342, signal names which can be selected are displayed below the signal selection unit 34, a signal name of a signal which should be displayed as a frequency characteristic graph is clicked on by operating a mouse cursor 33 or a keyboard, whereby a desired signal can be selected. It is also possible to select a plurality of signals to be graph-displayed. In that case, it may be possible to display correspondingly to the legend 322 by displaying with another line type in the domain of or to display the same number of graphs as the number of signals selected in the domain of the frequency characteristic display graph 321 for drawing different signals on the respective graphs.

In the domain for displaying types of the frequency characteristic in the above-described 3), there is displayed an ordinate selection unit 35 which is displayed as a frequency parameter setting screen. In the ordinate selection unit 35, there is displayed a selection button for selecting power, amplitude, a real number, an imaginary number, an absolute value and the like, which can be allocated as an ordinate to be graph-displayed. Display of an adequate ordinate is selected through the use of a selection button to match with selection of a signal to be graph-displayed. Here, an example in which amplitude of oxy-Hb has been selected is shown.

In the domain for determining a range of passing frequency of the band pass filter in the above-described 4) there are provided a low-frequency passing frequency display unit 361 and a high-frequency passing frequency display unit 362 of the band pass filter 1, and a low-frequency passing frequency display unit 363 and a high-frequency passing frequency display unit 364 of the band pass filter 2. These display values can be increased and decreased by a predetermined numerical width by clicking on a toggle switch provided adjacent to the display unit by a mouse cursor 33. In a process of setting numerical values of the respective band pass filters, a domain corresponding to a frequency range displayed on the passing frequency display unit is superimposed on the display of the frequency characteristic display graph 321 for being displayed. In the example of FIG. 4, adequate rectangular domains of ranges 365 and 366 sandwiched by a dot-and-dash line which correspond to the low-frequency passing frequency of the band pass filter 1 and the band pass filter 2 are displayed with color different from color of the background. These numerical information can be changed by moving a border line of the range 365 or 366 indicated by a dot-and-dash line by the mouse cursor 33. In this case, correspondingly thereto, the numerical values of the display units 361 to 364 are changed. When setting of two band pass filters is completed, a band pass filter to be applied is selected. This is executed by clicking on display 371 or 372 of the selection switch 1 or 2. In order to point out explicitly the band pass filter selected, color of the rectangular domain displayed superimposed on the displayed frequency characteristic display graph 321 will be made different from that of the background only for the band pass filter selected. Further, the selection switch 1 or 2 can be displayed with a black dot as display 371 or 372. Instead of indicating the range of the band pass filter by a rectangular domain having different color from the background, it is also good to indicate by enclosing with a line of a rectangular domain. In this case, in order to point out explicitly the band pass filter selected, it may be possible not to display a line of a rectangular domain corresponding to a band pass filter not selected or to change into a different line type or color. In the figure, since the second band pass filter has been selected, a black dot is displayed at the center of display 372 of the selection switch 2.

In the domain for selecting a filter when a plurality of band pass filters have been set in the above-described 5), there are provided an addition button 381, a delete button 382 and an application button 383. When setting a plurality of band pass filters or deleting a band pass filter set, it is performed by operating the addition button 381 and the delete button 382. The addition button 381 is depressed, whereby on the frequency characteristic display graph 321, a rectangular domain indicating a range of the band pass filter is newly displayed, further on the display portion of the high and low passing frequency display unit, new high and low frequency passing frequency display units are additionally displayed and even on the selective display unit for displaying the band pass filter selected, there is newly added a selective display unit. The newly added display will be operated so as to become predetermined setting. On the other hand, when deleting the band pass filter, in order to identify the band pass filter to be deleted, one portion of the display of the band pass filter is selected and thereafter it is deleted by depressing the delete button 382. For example, a rectangular domain indicating a range of the band pass filter which is displayed on the frequency characteristic display graph 321 will be selected and be deleted by depressing the delete button 382. As a result, the high and low frequency passing frequency display units corresponding to the band pass filter, one portion of display of which has been selected, the rectangular domain indicating a range of the band pass filter, and the selective display unit will be erased from the screen. After the operation of the addition button 381 and the delete button 382, the application button 383 is depressed, whereby change procedures of addition and deletion are completed, and a numerical range of the band pass filter set is decided to be stored within the memory of the living body light measuring device 13.

The button for closing a setting screen of the band pass filter in the above-described 6) is provided side by side with the addition button 381, the delete button 382 and the application button 383. After processing of addition or deletion, and further the operation of the application button 383, the closing button 384 is depressed, whereby the screen displayed in FIG. 4 is closed. In this case, when the closing button 384 is depressed without depressing the application button 383, it is advisable to display a comment for requesting the application button 383 to be depressed because the value of the band pass filter which has been set will not be reflected in the processing hereafter.

As the button for selecting whether the band pass filter will be automatically set by automatically operating an adaptive filter on the basis of a preset value or it will be set arbitrarily by the operator, in the above-described 7), there are provided an automatic setting button 391 and a manual setting selection button 392. When the automatic setting button 391 has been selected, a band pass filter which has been set in advance in a signal processing device of the living body light measuring device 13 will be automatically set. When the manual setting selection button 392 has been selected, the band pass filter will be adjusted and set in accordance with the above-described procedure. It will be determined by the selection of the switches 391 and 392 by which it will be set. The figure shows a state in which the manual setting selection button 392 has been selected.

FIG. 5 will be described in detail. The screens of FIG. 5 show results obtained by allowing a signal to be obtained from the optical fibers $12_2$ for light convergence to pass through the band pass filter set in FIG. 4. In the set screen of the band pass filter, in interlock with numerical values of the low and high frequency passing frequency display units 361 to 364 or changes of the rectangular domains indicating ranges 365 and 366 of the band pass filter, a time series graph 42 within a time series display screen 41 changes. Positions of a plurality (in the present embodiment, 24) of time series graphs 42 are arranged correspondingly to positions corresponding to the measurement positions exemplified in FIG. 2. The legend 43 shows correspondence between signals to be displayed and line types. Also, on a measurement condition display unit 44, there are shown measurement conditions. A signal display selection unit 45 selects a signal to be displayed as a graph.

In this case, in the screen of FIG. 4, a range of the passing band is determined, and a signal which has passed through the passing band is displayed on the screen of FIG. 5, and it is easy to use and good for the operator to display the screens of FIGS. 4 and 5 side by side on the same screen at the same time. In other words, when the operator arbitrarily changes the range of the filter in accordance with the subject while looking at the screen of FIG. 4, this influence is reflected on the screen of FIG. 5, and therefore, it becomes possible to confirm immediately whether or not the change is appropriate. Parallel display of this screen enables the operator to try several conditions easily.

Next, with reference to FIGS. 8 and 9, the detailed description will be made of handling of body movement component to be contained in a detected signal.

For a body movement criterion value of judgment, on the basis of which a detected signal is judged to contain body movement noise, a preset value is normally used, but there may be cases where the need for setting manually arises. For example, a case where it is outside a device constant that has been assumed, or a signal of the subject is outside the assumption. At this time, manual setting will be performed by a body movement criterion of judgment display setting screen 71. On the body movement criterion of judgment display setting screen 71, there are provided a body movement criterion value of judgment display graph 731, a body movement value of judgment input screen 74, an automatic setting selection switch 721, a manual setting selection switch 722, an application button 51, and a closing button 752. Selection of the manual setting or the automatic setting can be switched by selecting either the switch 721 or 722. If the automatic setting selection switch 721 has been selected, for the body movement criterion value of judgment, a preset value will be set. If the manual setting selection switch 722 has been selected, it becomes possible to set manually. Also, even by clicking on the body movement criterion value of judgment display graph 731 or the body movement value of judgment input screen 74 with the mouse cursor 75 on the screen 71, it is possible to switch an automatic setting selection unit 71 into a manual setting selection unit 72. This switching enables manual data input to the body movement criterion value of judgment display graph 731 and the body movement value of judgment input screen 74.

The body movement value of judgment input screen 74 is composed of a signal selection unit 741 for selecting the type of a signal to be used for judgment, a time input unit 742 for setting the body movement criterion value of judgment, and a criterion value input unit 743. On the signal selection unit 741, there is displayed a pull down for selecting a signal to be displayed on the body movement criterion value of judgment display graph 731 as in the case of the signal selection unit 34 on the frequency parameter setting screen described in FIG. 4.

On the body movement criterion value of judgment display graph 731, there is displayed a signal selected in the signal selection unit 741, but is drawn on the basis of a numerical value (time width for calculating a difference value) inputted in the time input unit 742. Also, in this graph, at a position of a numerical value (amount of signal alteration for each time width designated by a numerical value inputted by the time input unit 742) inputted in the criterion value input unit 743, there is drawn a body movement criterion value of judgment display bar 732. In this case, the ordinate of the body movement criterion value of judgment display graph 731 represents a frequency, and the abscissa represents an amount of signal alteration of a time series signal designated for each arbitrary time width. A statistic of this frequency distribution is displayed on a statistic display unit 733. If a peculiar value (where the frequency changes suddenly) is clearly observed against the smooth frequency distribution as shown in the present embodiment, such a peculiar value is not clearly observed in many instances although this statistic is not so necessary. At that time, on the assumption that this frequency distribution is a normal distribution, the criterion value can be determined with a dispersion ($\sigma$) as a standard. For example, a value corresponding to $3*\sigma$ is selected, and this value can be inputted into the criterion value input unit 743 for setting. In this respect, it has been described already that by inputting a numerical value into the criterion value input unit 743, the position of the body movement criterion value of judgment display bar 732 is changed. Conversely, the body movement criterion value of judgment display bar 732 is moved through the use of the mouse cursor 75, whereby the numerical value of the criterion value input unit 743 also changes. These two operate completely in synchronization.

In this respect, even in FIG. 8, the closing button 752 is depressed as in the case of FIG. 4, whereby the screen displayed in FIG. 8 is closed. In this case, when the closing button 752 is depressed without depressing an application button 751, it is advisable to display a comment for requesting the application button 751 to be depressed because the body movement criterion value of judgment which has been set will not be reflected in the processing hereafter.

FIG. 9 will be described in detail. FIG. 9 is a view showing a time domain signal display screen responsive to the body movement criterion value of judgment according to the present invention, and displays results obtained by applying the body movement criterion value of judgment which has been set in FIG. 8 to a signal to be obtained from the optical fibers $12_2$ for light convergence. In interlock with the value which has been set in the display setting screen 71 of the above-described body movement criterion value of judgment, a time series graph 82 within a time series display screen 81 changes. Positions of a plurality (in the present embodiment, 24) of time series graphs 82 are arranged correspondingly to positions corresponding to the measurement positions exemplified in FIG. 2. Concerning the setting of frequency characteristic, the description has been previously made of the fact that FIGS. 4 and 5 are displayed in parallel on the same screen, whereby it is possible to provide facilities for the operator, and the display setting screen 71 of the body movement criterion value of judgment of FIG. 8 and the time series display screen 81 of FIG. 9 are also displayed in parallel on the same screen. By doing so, it is possible to immediately confirm the effect of a value which has been set on display setting screen 71 of the body movement criterion value of judgment through the use of the graph of time series display screen 81. As a result, it becomes possible to immediately evaluate the body movement criterion value of judgment, and the setting can be easily and properly performed.

Even in the time series display screen 81 shown in FIG. 9, the legend 87 shows the correspondence between signals to be displayed and line types as in the case of FIG. 5. Also, a measurement condition display unit 88 displays conditions of measurement. In a signal display selection unit 85, a signal to be displayed as a graph will be selected.

A time series graph 82 to be displayed on a time series display screen 81 shown in FIG. 9 is capable of displaying results of each stimulus block in which addition and averaging are not performed, and results in which addition and averaging have been performed. When the results of each stimulus block in which addition and averaging are not performed are displayed, a stimulus block display selection unit 831 is selected, and thereafter a number of a stimulus block to be displayed is inputted into a display stimulus block value input unit 832 to display a graph of the number. When six stimulus blocks have been set during measurement as shown in FIG. 6, '6' is displayed on a total stimulus block number display unit 833. When an addition and averaging display unit 834 has been selected, the addition and averaging result is displayed. The figure shows a case where the addition and averaging display selection unit 834 has been selected.

It is selected by a selection unit with body movement noise removal 841 and a selection unit without body movement noise removal 842 whether or not a graph to be displayed contains body movement noise. When the stimulus block display selection unit 831 has been selected, however, selection of this selection unit with body movement noise removal 841 or the selection unit without body movement noise removal 842 does not make sense, and therefore, these cannot be selected. However, it is effective to display presence or absence of body movement noise (judgment result of body movement noise) within each graph by displaying color of the line in red when a stimulus block which has not been added and averaged to be displayed is judged to contain body movement noise, and displaying color of the line in blue when it is judged to contain no body movement noise or things like that. Of course, it may be possible to change the background color. Also, the type of a signal to be displayed as a graph can be selected by a signal selection unit 85. Further, as the ordinate of each graph, an absolute value and statistic of the signal can be used. For these selections, switching can be made between an absolute value selection unit 851 and a statistic selection unit 852.

Second Embodiment

In the first embodiment, the description has been made of an embodiment where a stimulus to be given to the subject has been programmed in advance, but in the second embodiment, the description will be made of an embodiment where the signal processor shown in the first embodiment is used; and during measurement, feed-back on its signal processing result is applied to the stimulus control unit 15 in real time; and a number of times (a number of times of a stimulus presented) for giving the stimulus or time for giving the stimulus (time of the stimulus presented) is changed. Since the structure of the device is the same as in the first embodiment, FIG. 1 can be referred to.

Figure 10:
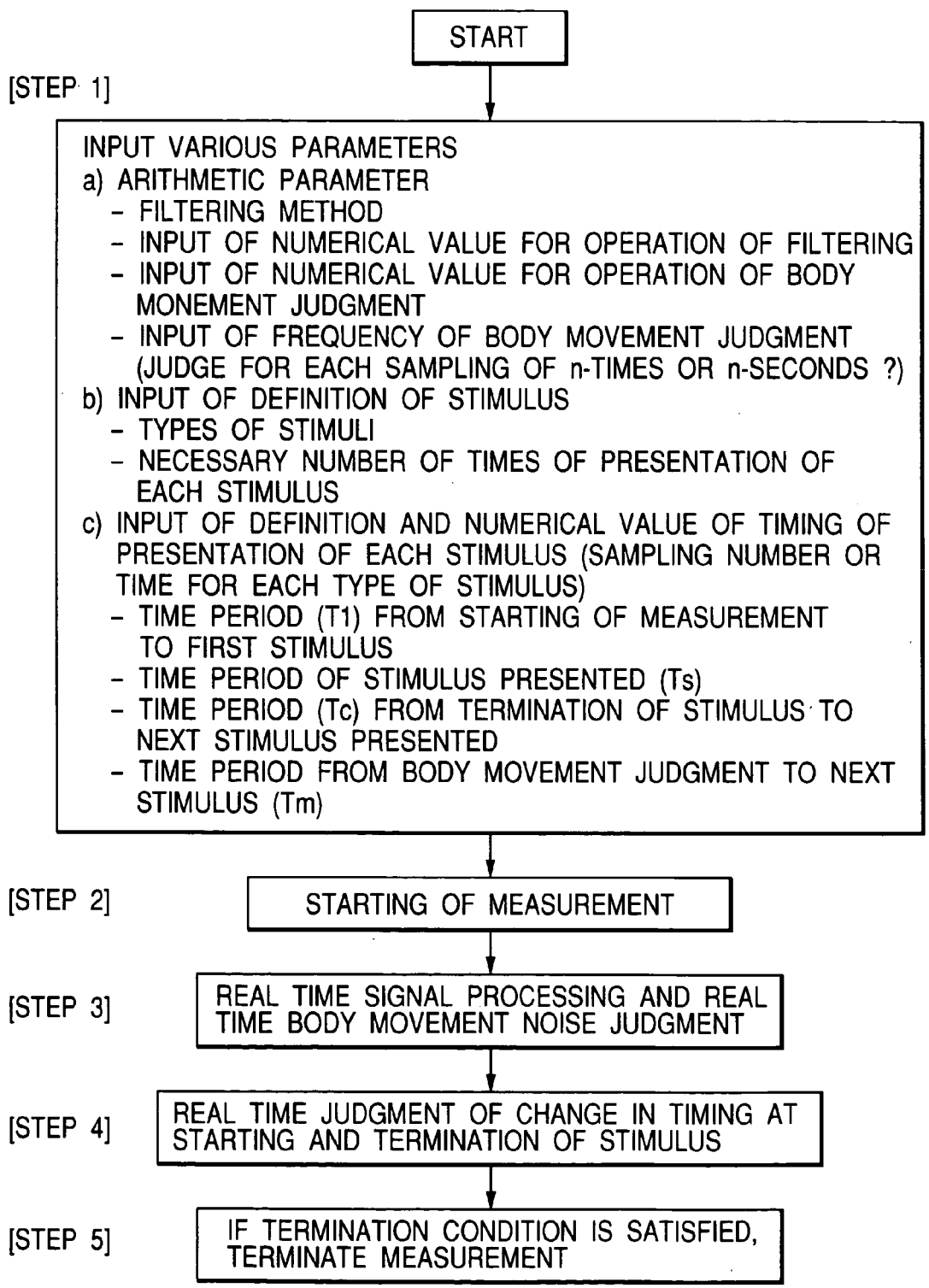
FIG. 10 is a view showing a flow of measurement of the second embodiment according to the present invention.

FIG. 10 shows a flow of measurement of the second embodiment according to the present invention.

[First Step]: Before measurement, numerical values or methods required for measurement signal processing will be inputted. These are broadly divided into the following three input items. That is, a) arithmetic parameter, b) stimulus definition input, and c) input of each timing (time) of stimulus presented definition numerical values. Each of these is specifically as below. These input values will be inputted for setting as initial input through the use of screens corresponding to items described in the first embodiment respectively.

a) Arithmetic parameter:
  Band pass filtering method,
  Input of arithmetic numerical values of the band pass filtering,
  Input of arithmetic numerical values for body movement judgment,
  Input of frequency of body movement judgment (to be judged for each sampling for n-times or n-seconds)

b) Stimulus definition input:
  Types of stimuli (If there are plural types of stimuli, each stimulus will be given a name)
  A number of times of stimulus presented (Ns) required for being measured without containing body movement noise to each of the above-described stimuli inputted,
  Definition of stimulus block. One stimulus block is defined by arbitrary pre-stimulus time Tpre, arbitrary stimulus time Ts and arbitrary post-stimulus time Tpost (See FIG. 6A).

c) Input of definition numerical values for each timing (time) of stimulus presented:
  Designate sampling number or time, and define every type of each stimulus.
  Input time (T1: constant) between commencement of measurement and the first stimulus.
  Time of stimulus presented of each stimulus (Ts: time may be different for each stimulus)
  Time between each stimulus terminated and next stimulus presented (Tc: time may be different for each stimulus)
  Minimal time between body movement judgment and next stimulus (Tm: constant).

[Second Step]: Commence measurement.

[Third Step]: Operate the measurement signal in real time to convert into various signals. The body movement judgment is performed for each n-sample or n-seconds that has been set in [First Step].

[Fourth Step]: When the body movement noise has been detected in the third step, stimulus terminated timing, next stimulus start timing and the number of times of stimulus presented will be changed. This information will be fed to the stimulus control unit 15 shown in FIG. 1 to apply feed-back to the actual stimulus.

In this case, a control processing method for feed-back according to the present invention is constituted by two functions. A first function is to add or change the number of times of stimulus during measurement, and a second function is to change, when body movement noise has been detected, the next stimulus starting time on the basis of a parameter given in advance during measurement.

Figure 11A:
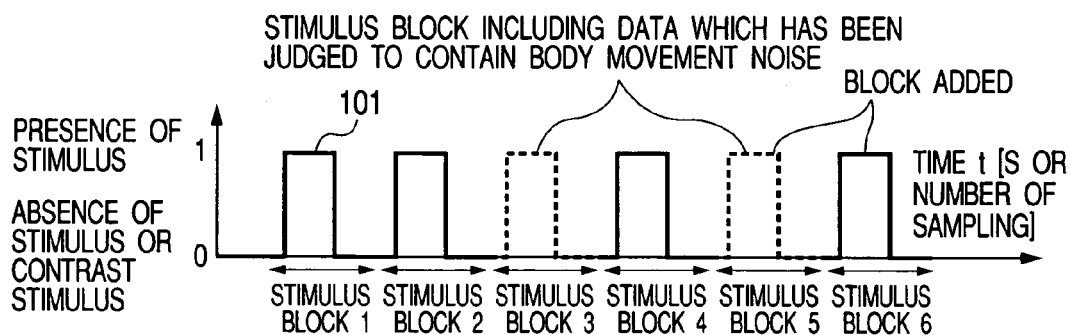
FIG. 11A and FIG. 11B are graphs showing an example of timing of stimuli to be actually given during measurement, and an example of timing of stimuli to be used for arithmetic evaluation of the result respectively, for explaining a first function of a control processing method for feedback of the second embodiment.
Figure 11B:
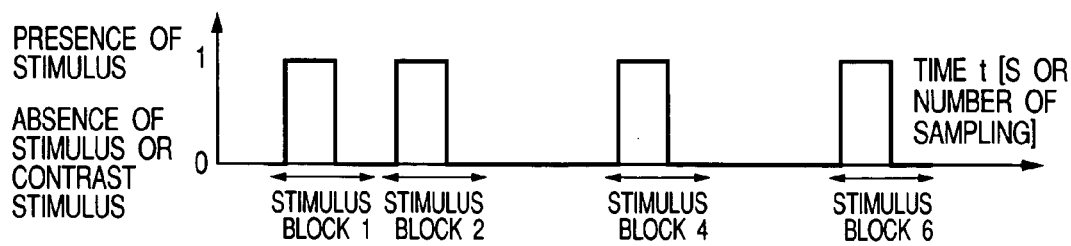

First, with reference to FIG. 11, the description will be made of this first function. In FIGS. 11A and 11B, there are displayed two types of graphs: actual stimulus timing to be given during measurement, and stimulus timing to be used for arithmetic evaluation of the result. In these graphs 11A and 11B, stimulus timing waveform 101 is displayed with time or a number of sampling taken on the abscissa, and with a time period in which no stimulus is given, or with a time period of contrast stimulus as 0 and that of stimulus as 1 on the ordinate. Therefore, as the measurement advances, stimulus blocks (set in the first step) will be increased in order. In this case, within the stimulus timing waveform 101, in order to point out explicitly a difference between a stimulus block including data judged to contain no body movement noise and a stimulus block including data judged to contain body movement noise, the stimulus block without body movement noise has been displayed by a solid line while the stimulus block containing body movement noise has been displayed by a dotted line. Therefore, the graph A shows that body move noise has been detected during the time period of the stimulus block 3 and the stimulus block 5 during measurement. In this embodiment, in the step 1, a number of times of stimulus including no body movement noise necessary for the operation has been set to Ns=4 times, but since the stimulus block 3 cannot be used for arithmetic evaluation of the result, if body movement noise is detected during the time period of the stimulus block 3, a signal will be transmitted to the stimulus control unit 15 shown in FIG. 1 so as to automatically add the number of times of stimulus presented once during measurement. Since the measurement advances and body movement noise has been detected again in the stimulus block 5, the signal will be transmitted to the stimulus control unit 15 so as to automatically add the number of times of stimulus presented once similarly. Since finally Ns=4 times is to be met at a point of time whereat the stimulus has been presented six times, the measurement will be terminated.

For the arithmetic evaluation of the result, any other stimulus blocks than the stimulus block 3 and the stimulus block 5 will be used. The stimulus block to be actually used for the arithmetic evaluation and its timing are displayed in the graph B.

Figure 12A:
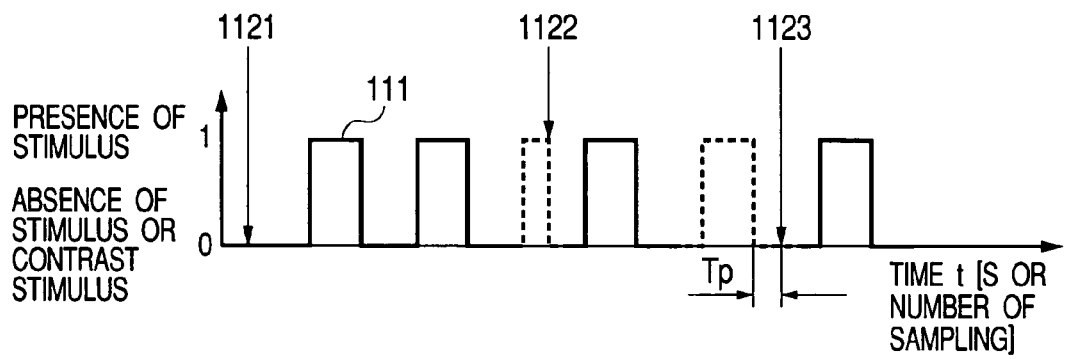
FIG. 12A and FIG. 12B are graphs showing an example of timing of stimuli to be actually given during measurement, and an example of timing of stimuli to be used for arithmetic evaluation of the result respectively, for explaining a second function of a control processing method for feedback of the second embodiment.
Figure 12B:
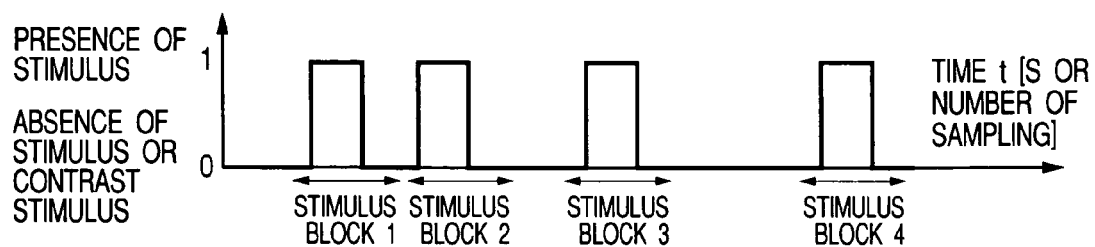

Next, with reference to FIG. 12, the description will be made of the second function. In FIGS. 12A and 12B, there are displayed the following two types of graphs: stimulus timing to be actually given during measurement, and stimulus timing to be used for arithmetic evaluation of the result. In these graphs 12A and 12B, stimulus timing waveform 111 is displayed with time or a number of sampling taken on the abscissa, and with a time period in which no stimulus is given, or with a time period of contrast stimulus as 0 and that of stimulus as 1 on the ordinate.

First, the basic function of this function is to change the stimulus timing predetermined if body movement noise is detected during measurement. If body movement noise is actually detected, a discontinue signal of the stimulus under execution currently and a signal for setting the time of next stimulus presented will be transmitted to the stimulus control device 15 shown in FIG. 1 (however, if body movement noise is detected during no stimulus or contrast stimulus, no signal for discontinuing the stimulus will be transmitted). Since, however, a time period T1 (constant) between commencement of measurement to be set in the step 1 and the first stimulus is used to operate a base line of the signal as described in the first embodiment, and a time period Tc between termination of each stimulus and the next stimulus presented or a minimal time period Tm between body movement judgment and the next stimulus can be regarded as mitigation time until a change in signal occurs because of stimulus presented or body movement is returned to the original state, it cannot be said to be appropriate to present the next stimulus immediately after body movement noise is detected. Therefore, it is effective to properly select a time period between when the body movement noise has been detected and commencement of the next stimulus in accordance with timing at which the body movement noise has been detected.

The timing at which the body movement noise is detected has the following three:
(a) When detected before the commencement of the first stimulus (detection timing 1121 of body movement noise)
(b) When detected during the stimulus time period (detection timing 1122 of body movement noise)
(c) When detected during no and contrast stimulus time period (detection timing 1123 of body movement noise).

By further subdividing the conditions for each timing, a time period between the body movement noise detected and commencement of the next stimulus can be determined. Time T1, Tm and Tc used in the following description have been set in the step 1, and time Tp represents a time period until the body movement noise has been detected since the stimulus is terminated, and is monitored at all times while the subject is measured.

(a) When detected before commencement of the first stimulus:
Condition 1: When T1>Tm, a time period until commencement of the next stimulus after body movement noise is detected will be set to T1.
Condition 2: When T1ϕTm, a time period until commencement of the next stimulus after body movement noise is detected will be set to Tm.
(b) When detected while the stimulus is given:
Condition 1: When Tc>Tm, a time period until commencement of the next stimulus after body movement noise is detected will be set to Tc. As soon as body movement noise is detected, the stimulus will be stopped immediately.
Condition 2: When TcϕTm, a time period until commencement of the next stimulus after body movement noise is detected will be set to Tm. As soon as body movement noise is detected, the stimulus will be stopped immediately.
(c) When detected during no and contrast stimulus time period:
Condition 1: When Tc>Tm, assuming an elapsed-time until body movement noise is detected since the stimulus is stopped to be Tp, Condition 1-1: When Tc−Tp>Tm, a time period until the next stimulus commences after body movement noise is detected will be set to Tc−Tp. In other words, the time period until the predetermined next stimulus commences will not be changed.
Condition 1-2: When Tc−TpϕTm, a time period until the next stimulus commences after body movement noise is detected will be set to Tm.
Condition 2: When TcϕTm, a time period until commencement of the next stimulus after body movement noise is detected will be set to Tm.

When merits of the subject are taken into account, it is preferable to terminate the measurement within as short a time as possible, and as a second point of the feed-back control processing method, it is effective to shorten the measurement time because useless stimulus which cannot be used to process a signal is discontinued.

[Step 5]: At a point of time whereat the necessary number of times of stimulus presented including no body movement noise of each stimulus that has been set in the step 1 has reached Ns, the measurement will be terminated.

By this control processing flow, it is possible to realize obtaining signals having the same number of times of stimulus for each measurement or for each subject, and it becomes possible to compare plural measurements as a homogenous statistic.

It becomes possible to measure the cerebral function of subjects such as newborn babies incapable of voluntarily controlling the body movement.

What is claimed is:
1. A living body light measuring device comprising:
a light irradiating source for irradiating light into a living body which is a subject of study;
a light condensing detector for condensing living body passage light for detection when light irradiated by said light irradiating source passes through the interior of said living body,
a stimulus device wherein a stimulus is intermittently provided to said subject;
a noise detector from which on the basis of detected noise associated with body movement of said subject in said living body passage light detected, a direction is given to the stimulus device to control a stop and start of the stimulus applied and to control a number of times of said stimulus to be given to said subject which has been programmed in advance and said stimulus application is changed based on the movement of the subject.

2. The living body light measuring device according to claim 1, further comprising:

a band pass filter for causing said measured signal to pass through a predetermined frequency band, a display screen for inputting a parameter which sets said frequency band of said band pass filter, and where on said display screen, a frequency characteristic of said signal is also displayed at the same time when said band of said band pass filter is set to aid in setting the frequency band of the band pass filter.

3. The living body light measuring device according to claim 1, wherein from an amount of change in an arbitrary time interval in a time domain of a value corresponding to an amount of change in hemoglobin concentration or a change in hemoglobin concentration of said measured signal measured within unit time, a noise level associated with body movement which a signal measured is determined.

4. The living body light measuring device according to claim 3, further comprising:

a criterion value parameter for judging a noise level associated with body movement present in said signal measured;

a graph for representing a characteristic of said criterion value parameter; and a display screen for displaying a statistic of said characteristic.

5. A living body light measuring device comprising:

a light irradiating source for irradiating light into a living body which is a subject of study;

a light condensing detector for condensing living body passage light to be obtained, for detection, when light irradiated by said light irradiating source passes through the interior of said living body, a stimulus device from which a stimulus is intermittently given to said subject, and on the basis of noise associated with body movement of said subject in said living body passage light detected by said detector a number of times of a stimulus to be given to said subject which has been programmed in advance will be changed.

6. The living body light measuring device according to claim 5, further comprising:

a band pass filter for causing said measured signal to pass through a predetermined frequency band, a display screen for inputting a parameter which sets said frequency band of said band pass filter, and where on said display screen, a frequency characteristic of said signal is also displayed at the same time when said band of said band pass filter is set to aid in setting the frequency band of the band pass filter.

7. The living body light measuring device according to claim 5, wherein from an amount of change in an arbitrary time interval in a time domain of a value corresponding to an amount of change in hemoglobin concentration or a change in hemoglobin concentration of said measured signal measured within unit time, a noise level associated with body movement which a signal measured is determined.

8. The living body light measuring device according to claim 7, further comprising:

a display screen for setting a criterion value for judging a noise level associated with body movement present in said signal measured;

and a display screen for displaying a signal graph in the time domain in which said criterion value is reflected in real time.

9. A method for controlling the timing of sound stimulus in an optical imaging system used to image a living body of a subject under study comprising:

setting a predetermined number of sound stimulus applications to be applied over a time period to a subject sufficient to produce a measurement signal from optical radiation applied to the subject which is directed into the subject's body and detected by a detector and which shows the subject's reaction to the sound stimulus;

detecting in a detector whether said subject's body makes a movement by detecting noise in said measurement signal;

stopping the stimulus if body movement noise is detected in the measurement signal by sending a discontinue signal of the sound stimulus under execution currently; and sending a signal for setting the time of the next sound stimulus to be transmitted to a stimulus control device;

wherein a time period between termination of each sound stimulus and the next sound stimulus presented is adjusted to be a minimal time period to provide a movement free measurement signal in a minimum amount of time including the predetermined number of sound stimulus applications to be applied because no useless sound stimulus time is expended when the subject is moving and is not stabilized.

* * * * *